United States Patent [19]
Haddon

[11] Patent Number: 5,958,334
[45] Date of Patent: Sep. 28, 1999

[54] COMBINATION CAPABLE OF FORMING AN ODOR BARRIER AND METHODS OF USE

[76] Inventor: Bruce Alexander Haddon, 50 Chisolm Avenue, Clareville, New South Wales 2107, Australia

[21] Appl. No.: 08/652,598
[22] PCT Filed: Dec. 13, 1994
[86] PCT No.: PCT/AU94/00768
   § 371 Date: Sep. 24, 1996
   § 102(e) Date: Sep. 24, 1996
[87] PCT Pub. No.: WO95/16470
   PCT Pub. Date: Jun. 22, 1995

[30]   Foreign Application Priority Data

Dec. 13, 1993  [AU]  Australia ............................. PM 2949

[51] Int. Cl.$^6$ ...................................................... A61L 9/00
[52] U.S. Cl. ........................... 422/5; 422/122; 424/76.5; 424/76.6
[58] Field of Search ...................... 422/5, 122; 424/76.5, 424/76.6

[56]   References Cited

U.S. PATENT DOCUMENTS

| | | | |
|---|---|---|---|
| 2,998,390 | 8/1961 | Hamilton | 422/5 X |
| 3,107,216 | 10/1963 | Hamilton | 422/5 X |
| 3,208,936 | 9/1965 | Hamilton | 422/5 X |
| 3,383,710 | 5/1968 | Sumner | 4/1 |
| 3,762,875 | 10/1973 | Burmeister | 422/5 X |
| 4,007,262 | 2/1977 | Bowers | 424/76 |
| 5,071,622 | 12/1991 | Dunson, Jr. | 422/5 |

FOREIGN PATENT DOCUMENTS

87/06289  10/1987  WIPO .

OTHER PUBLICATIONS

Ash, Michael and Irene, The Handbook of Cosmetic and Personal Care Additives, p. 184, 1994.

*Primary Examiner*—Krisanne Thornton
*Attorney, Agent, or Firm*—Foley & Lardner

[57]   ABSTRACT

A solid combination of compounds capable of being packaged in a single, air tight container, and capable of forming an odor barrier for trapping/blocking odors, especially in relation to a toilet, urinal or other aqueous based waste container/vehicle/pipe/drain is provided, as is a method for its use. The combination comprises (i) a first component comprising an alkaline effervescent compound in solid form, (ii) a second component comprising an acid in solid form, and (iii) an oxidizing agent in solid form, and at least one of the first component and second components comprise a stable foam-forming surfactant in solid form. The first component reacts with the second components to form a stable foam odor barrier which traps/blocks odors.

33 Claims, 2 Drawing Sheets

COMBINATION CAPABLE OF FORMING AN ODOR BARRIER AND METHODS OF USE

TECHNICAL FIELD

This invention relates to a combination capable of forming an odour barrier for trapping/blocking odours, more particularly to a toilet odour barrier. The invention also relates to methods for trapping/blocking odours, a receptacle and method of using the receptacle.

BACKGROUND ART

All present methods of bathroom deodorising either cover up the bad air (aerosol perfume spray) or try to increase air replacement (exhaust fans). Variations include perfume dispensers located around the toilet rim activated by the flush, toilet "blue" in the holding tank which foams slightly after flushing. However, the foam is produced after the odour has already been released and after the fecal matter is flushed away.

The cistern is an attempt to prevent the spreading of odours by trapping the human waste under the water for the period before it is flushed away. They cannot work as designed because more fibre in the Western diet makes faeces float on top of the water, facilitating transfer of odours to the surrounding air.

Portable chemical toilets partly solve the problem by using liquids that are lighter than water, increasing the likelihood of solid waste sinking and being isolated. Some use a spring trapdoor which re-closes after defecation to isolate collected waste. These options are not appropriate for the bathroom.

There are certain natural non-flushing toilets which use a permanent fan to produce negative pressure under the seat. They are very effective in eliminating smells from the bathroom but are more for rural settings since they transfer the smell outside.

There is a need for using an airlock to isolate human waste from the surrounding air in the bathroom.

OBJECTS OF INVENTION

It is an object of this invention to provide a combination capable of forming an odour barrier for trapping/blocking odours. It is a further object of this invention to provide methods for trapping/blocking odours. It is a further object of this invention to provide a receptacle and method of using the receptacle.

DISCLOSURE OF INVENTION

According to a first embodiment of this invention there is provided a combination capable of forming an odour barrier, the combination comprising at least two components wherein the first component is capable of reacting with the second component to form an odour barrier capable of trapping/blocking odours about a medium selected from the group consisting of an odour containing/releasing medium and a medium to receive odour containing/releasing material.

Typically the first component is capable of reacting with the second component, on addition of the first and second components to the medium, to form the odour barrier capable of trapping/blocking odours about the odour containing/releasing medium or the medium to receive odour containing/releasing material.

According to a second embodiment of this invention there is provided a method of trapping/blocking odours comprising forming an odour barrier about a medium selected from the group consisting of an odour containing/releasing medium and a medium to receive odour containing/releasing material, to form a barrier to odours from the medium.

Since the combination is capable of forming an odour barrier for trapping/blocking odours it effectively acts as a deodoriser. The odour barrier is capable of trapping/blocking odours or preventing odours from substantially penetrating the barrier. Typically the method comprises adding to the odour containing/releasing medium or the medium to receive odour containing/releasing material an effective barrier forming amount of a combination capable of forming an odour barrier for trapping/blocking odours, the combination comprising at least two components wherein the first component is capable of reacting with the second component, on addition of the first and second components to the medium, to form an odour barrier capable of trapping/blocking odours about the odour containing/releasing medium or the medium to receive odour containing/releasing material.

The combination of the invention is capable of forming a foam without external agitation (for example it does not require flushing).

Generally the barrier capable of trapping/blocking odours about a odour releasing medium is a foam, a gaseous layer or zone, a combination of a foam and a gaseous layer, more typically an odourless foam, an odourless gaseous layer or zone, an odourless liquid layer or zone or an odourless solid layer or zone. The foam generally floats on the odour containing/releasing medium or the medium to receive odour containing/releasing material thereby forming an odour barrier to odours emanating from the medium. Generally the medium is an aqueous based medium and the foam floats on the aqueous medium. The barrier may contain one or more perfumes or fragrances. Advantageously the barrier is an odourless foam (i.e. a foam that by itself does not substantially smell but which may optionally include substances that release smells such as perfumes and fragrances, for example). Typically the odour releasing medium is solid waste, liquid waste, gaseous waste or mixtures thereof. The invention is particularly useful in trapping/blocking odours in a toilet or urinal or other aqueous-based waste container/vehicle/pipe/drain. The combination of the invention is administered to a toilet bowl or urinal prior to defacation (usually just prior to use, eg immediately prior to use or 2 seconds–5 minutes, 5 seconds–3 minutes, 5 seconds–2 minutes, 10 seconds–1.5 minutes, 10 seconds–1 minute, 10 seconds–30 seconds, 10 seconds–45 seconds, prior to use and thus prior to flushing a toilet bowl or urinal). The foam formation is therefore not connected with or dependent on or concurrent with the flushing of a toilet bowl or urinal.

Examples of the first and second components are shown in Table 1:

TABLE 1

| FIRST COMPONENT | SECOND COMPONENT | REACTION |
| --- | --- | --- |
| (1) Component A | Component B | A + B → foam. |
| (2) Component $A_1$ + $S_1$ ($S_1$ = foam forming surfactant) | Component $B_1$ | $A_1 + B_1 \rightarrow G_1$ (gas). $G_1 + S_1 \rightarrow$ foam. |
| (3) Component $A_2$ | Component $B_2$ + $S_2$ ($S_2$ = foam forming surfactant) | $A_2 + B_2 \rightarrow G_2$ (gas). $G_2 + S_2 \rightarrow$ foam. |

TABLE 1-continued

| FIRST COMPONENT | SECOND COMPONENT | REACTION |
|---|---|---|
| (4) Component $A_3 + S_3$ ($S_3$ = foam forming surfactant) | Component $B_3 + S_{3a}$ ($S_{3a}$ = foam forming surfactant) | $A_3 + B_3 \rightarrow G_3$ (gas). $G_3 + S_3 + S_{3a} \rightarrow$ foam. |
| (5) Component $A_4 + S_4$ ($S_4$ = foam forming surfactant + foam promoting agent) | Component $B_4$ | $A_4 + B_4 \rightarrow G_4$ (gas). $G_4 + S_4 \rightarrow$ foam. |
| (6) Component $A_5 + S_5$ ($S_5$ = foam forming surfactant) | Component $B_5 + S_{5a}$ ($S_{5a}$ = foam promoting agent) | $A_5 + B_5 \rightarrow G_5$ (gas). $G_5 + S_5 + S_{5a} \rightarrow$ foam. |
| (7) Component $A_6 + S_6$ ($S_6$ = foam promoting agent) | Component $B_6 + S_{6a}$ ($S_{6a}$ = foam forming surfactant) | $A_6 + B_6 \rightarrow G_6$ (gas). $G_6 + S_6 + S_{6a} \rightarrow$ foam. |
| (8) Component $A_7 + S_7$ ($S_7$ = foam forming surfactant + foam promoting agent) | Component $B_7 + S_{7a}$ ($S_{7a}$ = foam promoting agent) | $A_7 + B_7 \rightarrow G_7$ (gas). $G_7 + S_7 + S_{7a} \rightarrow$ foam. |
| (9) Component $A_8 + S_8$ ($S_8$ = foam forming surfactant + foam promoting agent) | Component $B_8 + S_{8a}$ ($S_{8a}$ = foam forming surfactant) | $A_8 + B_8 \rightarrow G_8$ (gas). $G_8 + S_8 + S_{8a} \rightarrow$ foam. |
| (10) Component $A_9$ | Component $B_9 + S_9$ ($S_9$ = foam forming surfactant + foam promoting agent) | $A_9 + B_9 \rightarrow G_9$ (gas). $G_9 + S_9 \rightarrow$ foam. |
| (11) Component $A_{10} + S_{10}$ ($S_{10}$ = foam promoting agent) | Component $B_{10} + S_{10a}$ ($S_{10a}$ = foam forming surfactant + foam promoting agent) | $A_{10} + B_{10} \rightarrow G_{10}$ (gas). $G_{10} + S_{10} + S_{10a} \rightarrow$ foam. |
| (12) Component $A_{11} + S_{11}$ ($S_{11}$ = foam forming surfactant) | Component $B_{11} + S_{11a}$ ($S_{11a}$ = foam forming surfactant + foam promoting agent) | $A_{11} + B_{11} \rightarrow G_{11}$ (gas). $G_{11} + S_{11} + S_{11a} \rightarrow$ foam. |
| (13) Component $A_{12} + S_{12}$ ($S_{12}$ = foam forming surfactant + foam promoting agent) | Component $B_{12} + S_{12a}$ ($S_{12a}$ = foam forming surfactant + foam promoting agent) | $A_{12} + B_{12} \rightarrow G_{12}$ (gas). $G_{12} + S_{12} + S_{12a} \rightarrow$ foam. |

It will be appreciated from Table 1 that the first component may be a single integral component or may be split into a number of separate subcomponents and similarly the second component may be a single integral component or may be split into a number of separate subcomponents. It will also be appreciated that there are many variations and alternatives to those shown in Table 1.

Generally the first component and the second component (eg components $A-A_{12}$ and components $B-B_{12}$) include compounds which when mixed together produce a foam. The foam formation may be aided by a gas, generally an odourless, non toxic gas. The gas may be produced as a result of the mixing of the first component and the second component; (eg components $A-A_{12}$ and components $B-B_{12}$) or may be added to the mixture of the first component and the second component (eg a mixture as shown in Table 1 of components $A-A_{12}$ and components $B-B_{12}$). The gas produced is a non-toxic gas, or the amount of gas produced is a non-toxic amount. The first and/or second components may be liquids, solids or aerosols. Where the first and second components are in solid form they may be combined into a single mixture, such as a compressed powder or non compressed powder or non compressed granules or compressed granules, which may be subsequently added to an aqueous medium to form a foam. At least some of the powder or granules (eg 1–99 wt %, more typically 10–70 wt % and even more typically 25–50 wt %) may be coated with a slow release coating (eg polyvinylalcohol). Typically the first component or the second component (eg components $A-A_{12}$ or components $B-B_{12}$) is or includes an alkaline effervescent compound or an acid compound, provided that when the first component (eg $A-A_{12}$) is or includes an acid compound, the second component (eg $B-B_{12}$) is or includes an alkaline effervescent compound and when the second component (eg $B-B_{12}$) is or includes an acid compound the first component (eg $A-A_{12}$) is or includes an alkaline effervescent compound.

An alkaline effervescent compound is one that reacts with an acid to liberate a gas, typically carbon dioxide. Examples of alkaline effervescent compounds are sodium bicarbonate, potassium carbonate, ammonium bicarbonate, ammonium carbonate, sodium carbonate, and potassium bicarbonate and other water soluble carbonate and bicarbonate salts. Examples of acid compound are citric acid, tartaric acid, hydrochloric acid, sulphuric acid, nitric acid, oleic acid, boric acid, stearic acid, palmitic acid, glucuronic acid, alpha-hydroxybutyric acid, alpha-hydroxyisobutyric acid, mandelic acid, pyruvic acid, beta-phenyllactic acid, beta-phenylpyruvic acid, saccharic acid, tartronic acid, beta-hydroxybutyric acid, malic acid, citramalic acid, mucic acid, glycolic acid, hydroxyglutaric acid, lactic acid, catechol acid, oxalic acid, succinic acid, tartaric acid, salicyclic acid, adipic acid, ascorbic acid and any mixture thereof. Examples of components which when mixed together produce a gas are: sodium bicarbonate and hydrochloric acid; sodium bicarbonate and ascorbic acid; potassium bicarbonate and citric acid; sodium bicarbonate and citric acid; sodium bicarbonate and tartaric acid; ammonium bicarbonate and hydrochloric acid; ammonium bicarbonate and ascorbic acid; ammonium bicarbonate and citric acid; ammonium bicarbonate and tartaric acid; sodium carbonate and hydrochloric acid; sodium carbonate and ascorbic acid; potassium carbonate and citric acid; sodium carbonate and citric acid; sodium carbonate and tartaric acid; ammonium carbonate and hydrochloric acid; ammonium carbonate and ascorbic acid; ammonium carbonate and citric acid; ammonium carbonate and tartaric acid; or a mixture of sodium bicarbonate, potassium bicarbonate and potassium carbonate when combined with a mixture of or one of hydrochloric acid, sulphuric acid, ascorbic acid, tartaric acid, and citric acid. The amounts of acid and alkaline effervescent compounds used in the combination are adjusted so that they react to form carbon dioxide. Typically the acid and alkaline effervescent compounds are used in stoichiometric amounts (but they may also be used in non-stoichiometric amounts typically to adjust the pH of the liquid, eg to leave the water slightly alkaline, say pH 7.1–11.5).

The first component and the second component (eg components $A-A_{12}$ and components $B-B_{12}$) may include or may be chemicals that react to form a foam without a carbon dioxide generator. Examples are monoammonium phosphate and sodium bicarbonate, or aluminium sulphate and sodium bicarbonate.

Generally the amount of the first component and the second component (eg components $A-A_{12}$ and components $B-B_{12}$) used in the combination is 1 to 99 wt % or mole %, prefrably 5 to 80 wt % or mole %, more preferably 10 to 50 wt % or mole %, based on the total weight or moles of the combination.

The first and second components may independently in the form of solids or liquids (eg first component-solid, second component-solid, or first component-solid, second component-liquid, or first component-liquid, second component-liquid, or first component-liquid, second component-solid).

The first component and/or the second component (eg components $A-A_{12}$ and components $B-B_{12}$) used in the combination may where they are water soluble, be used in the form of aqueous solutions eg 0.01 to 90 vol %, wt % or mole %, preferably 0.5 to 70 vol %, wt % or moles %, more preferably 0.2 to 25 vol %, wt % or mole %, more preferably 1 to 15 vol %, wt % or mole %, based on the total volume, weight or moles of the solution. Typically the first and/or second components are used in concentrations in water in the range of 0.025M to 5M, 0.125M to 4M, 0.25M to 3.5M, 0.5M to 3M, 0.1M to 2M, 0.1M to 1.5M, 0.2M to 2M, 0.2M to 1.25M, 0.1M to 1M, 0.1M to 0.5M, 0.75–2.5M, 0.3M to 2.25M, and 0.2M to 0.75M.

Generally the foam forming surfactant is one which is a slow-draining and long-lived foam. Typically 0.1–90 wt %, vol % or mole %, more typically 0.5–70 wt %, vol % or mole %, even more typically 1–50 wt %, vol % or mole % even more typically 2–30 wt %, vol % or mole % of surfactant is used. The surfactants are generally anionic, cationic, amphoteric or nonionic. Mixtures of surfactants may be used but some surfactants are incompatible such as a mixture of anionic and cationic surfactants.

Examples of anionic surfactants are water-soluble soaps or water-soluble synthetic surface active compounds. Examples of the soaps are unsubstituted or substituted ammonium salts of higher fatty acids ($C_{10}$–$C_{22}$), such as the sodium or potassium salts of oleic acid or stearic acid or of natural fatty acid mixtures such as coconut oil or tallow oil, alkali metal salts, alkaline earth metal salts or fatty acid methyllaurin salts. Examples of synthetic surfactants are alkylarylsulphonates, sulphonated benzimidazole derivatives, fatty alcohol sulphates, or fatty alcohol sulphonates.

Examples of alkylarylsulphonates are the calcium, sodium, or triethanolamine salts of dodecylbenzenesulphonic acid, dibutylnaphthalenesulphonic acid, of a condensate of naphthalenesulphonic acid and formaldehyde or the phosphate salt of the phosphoric acid ester of an adduct of p-nonylphenol with 4 to 14 moles of ethylene oxide. Examples of sulphonated benzimidazole derivatives are 2 sulphonic acid groups and one fatty acid radical containing approximately 8 to 22 carbon atoms. Examples of fatty alcohol sulphates or sulphonates are unsubstituted or substituted ammonium salts such as $C_8$–$C_{22}$ alkyl radical including the alkyl moiety of acyl radicals such as the calcium or sodium salt of lignosulphonic acid, of a mixture of fatty alcohol sulphates from naturally occurring fatty acids, of dodecylsulphate, alkali metal salts or alkaline earth metal salts or the salts of sulphated and sulphonated fatty alcohol/ethylene oxide adducts.

Examples of non-ionic surfactants are polyglycol ether derivatives of aliphatic or cycloaliphatic alcohols having approximately 3 to 30 glycol ether groups and approximately 8 to 20 carbon atoms in the (aliphatic) hydrocarbon moiety; saturated or unsaturated fatty acids and alkylphenols having approximately 6 to 18 carbon atoms in the alkyl moiety of the alkylphenols; water-soluble adducts of polyethtylene oxide with ethylenediaminopolypropylene glycol, polypropylene glycol or alkylpolypropylene glycol having approximately 1 to 10 carbon atoms in the alkyl chain, having approximately 20 to 250 ethylene glycol ether groups and approximately 10 to 100 propylene glycol ether groups in the usual ratio of 1 to 5 ethylene glycol moiety: propylene glycol moiety; fatty acid esters of polyoxyethylene sorbitan such as polyoxyethylene sorbitan trioleate; octylphenoxypolyethoxyethanol; polyethylene glycol; tributylphenoxypolyethyleneethanol; polypropylene/polyethylene oxide adducts; castor oil polyglycol ethers; nonylphenolpolyethoxyethanols.

Examples of cationic surfactants are quaternary ammonium salts in the form of halides, methylsulphates or ethylsulphates which have as N-substituent at least one $C_8$–$C_{22}$ alkyl radical or unsubstituted or halogenated lower alkyl or benzyl or hydroxy-lower alkyl radicals, such as stearyltrimethylammonium chloride or benzyldi(2-chloroethyl) ethylammonium bromide.

Examples of amphoteric surfactants are the aminocarboxylic and aminosulphonic acids and salts thereof such as alkali metal 3-(dodecylamino)propionate and alkali metal 3-(dodecylamino)propane-1-sulphonate; alkyl and alkylamido betaines such as cocamidopropyl betaine; higher fatty alkanolamides having approximately 12 to 16 carbon atoms in the acyl group which is reacted with a lower (1 to 3 carbon atoms) mono- or dialkanolamine such as lauric monoethanolamide or cocodiethanolamide.

Examples of surfactants which may be used in the combination are surfactants from the TERIC® series such as N4 TERIC, N9 TERIC G9 A6 TERIC, wherein surfactants that form the TERIC® series are nonylphenol ethoxylate surfactants or the RHODAFAC® series such as RHODAFAC RA 600, RHODAFAC RA, wherein surfactants that form the RHODOFAC® series are phosphated alkyl ethoxylate surfactants or the EMPININ® series such EMPININ Q70 wherein surfactants that form the EMPININ® series are sodium fatty alcohol triethoxysulfate surfactants or the EMPILAN® series such as EMPILAN KM11, EMPILAN CME, wherein surfactants that form the EMPILAN® series are fatty alcohol ethoxylates, coconut monoethanolamides, coconut diethanolamides, and coconut isopropanolamides or the GARDIQUAT® series such as GARDIQUAT 1450, wherein surfactants that form the GARDIQUAT® series are alkylbenzyldimethyl ammonium chloride surfactants. Further examples are soap, sodium lauryl sulphate, or sodium cholate. Especially preferred surfactants are DECOL BD/80, and GEROPON T-77. GEROPON T-77 produces more foam but is less stable than DECOL BD/80 foam, but with foam stabiliser this surfactant gives a successful foam thick enough and stay long enough (10 minutes) to cover the bowl with a thickness of about 2 cm at the minute of the 10 minutes. Other preferred surfactant and sodium lauryl sulphate (eg. EMPICOL LZV/D, pellets, EMPICOL LZD as powder both from Albright and Wilson), sodium alkyl benzene sulphonate (eg. NANSA HS80/AP from Albright and Wilson, DECOL BD/80 from Harcros Industrial Chemical), and sodium methyl oleoyl taurate (GEROPON T-77 from Rhône-Poulenc).

Further examples of surfactants are described in "Encyclopedia of Chemical Technology", Kirk Othmer, 3rd edition, Volume 8, John Wiley & Sons 1982, "Handbook of Surfactants", M. R. Porter, Blackie (Glasgow and London), Chapman and Hall (USA) 1991, "Encyclopedia of Surfactants", compiled by Michael and Irene Ash, Volumes I–III, Chemical Publishing Co. 1980–1981. "Encyclopedia of Surfactants", compiled by Michael and Irene Ash, Volume IV, Chemical Publishing Co. 1985, "A Formulary of Detergents and Other Cleaning Agents", compiled by Michael and Irene Ash, Chemical Publishing Co. 1980, "Emulsifying Agents An Industrial Guide", Ernest W. Flick, Noyes Publications 1990, "What Every Chemical Technologist Wants to Know About . . . Volume IV Conditioners, Emollients and Lubricants", compiled by Michael and Irene Ash, Edward Arnold 1990, "McCutcheon's Detergents and Emulsifiers Annual", MC Publishing Corp., Glen Rock, N.J., USA, 1988 and "Tensid-Taschenbuch", H. Stache, 2nd edition, C. Hanser Verlag, Munich, Vienna, 1981, the contents of which are incorporated herein by cross reference. Typically more than one surfactant is used. Generally the amount of surfactant used in the combination is 0.5 to 99 wt %, preferably 20 to 90 wt %, more preferably 50 to 80 wt %, based on the total weight of the combination.

Typically the foam promoting agent is a frothing agent, foam stabiliser; thickening agent; a foam booster or mixture thereof; or any other component which is capable of promoting the formation of a foam.

Examples of frothing agents are short, branched-chain alcohols, such as, methyl isobutyl carbinol, 4-methyl-2pentanol, poly(propylene glycol) methyl ethers, glycerol, pine oil, cresylic acid or creosote. Examples of foam stabilizers are vegetable oils or epoxidised vegetable oils such as epoxidised coconut oil, rape oil, or soybean oil, or soaps, proteins, extract of licorice root, fatty acids or sulphite liquors. Examples of thickening agents are starch, sodium carboxymethyl cellulose, methocel, carboxy vinyl polymers, xanthan gum, magnesium aluminium silicates, methyl cellulose, natural gums, gum arabic, clays, soap gels, lipophilic fatty acid esters of alumina gel. Further examples of foam promoting agents are glycerine, glycerol, diglycerol, pinus Montana Needle Oil, Pine Needle Oil, saponins, or sodium cholate.

Foam boosters are generally added to increase the foam volume. Examples of foam boosters are cocamide, cocamidoethyl betaine, cocamidopropyl betain, cocamidopropyl hydroxysultaine, cocoamphodipropionic acid, coco-betaine, coco/oleamidopropyl betaine, coco-sultaine, cocoyl hydroxyethyl) imidazoline, polyvinylpyrrolidone (PVP), polyox, cetyl betaine, decyl betaine, DEA-cocamphodipropionate, DEA-lauraminopropionate, disodium isostearyl sulphosuccinate, isopropyl stearate, lauramide, lauramidopropyl betaine, lauryl betaine, lauryl sultaine, myristamidopropyl betaine, myristaminopropionic acid, myristyl betaine, oleamidopropyl betaine, oleamidopropyl hydroxysultaine, oleyl betaine, palmamidopropyl betaine, palmitamidopropyl betaine, PEG-6 cocamide, PEG-3 lauramide, PEG-5 lauramide, PEG-6 lauramide, sodium cocoamphoacetate, sodium cocoamphopropionate, sodium lauraminopropionate, sodium lauroamphopropionate, sodium lauroyl sarcosinate, sodium myristoamphoacetate, sodium myristoyl sarcosinate, TEA-hydrogenated tallow glutamate, TEA-lauraminopropionate, TEA-myristaminopropionate or undecylenamidepropylamine oxide.

Typically more than one foam promoting agent is used. Generally the amount of foam promoting agent used in the combination is 1 to 99 wt %, preferably 5 to 80 wt %, more preferably 10 to 50 wt %, based on the total weight of the combination.

An abherent (lubricant) may be further added to the combination to assist in the removal of solid waste. Examples of abherents include flour, talc, polytetrafluoroethylene, hydrocarbon wax, silicone oil, peanut oil, poly(vinyl alcohol), stearates or other like abherents. Further examples of abherents are described in "Encyclopedia of Chemical Technology", Kirk Othmer, 3rd edition, Volume 1, John Wiley & Sons 1982, the contents of which are incorporated herein by cross reference. Generally the amount of abherent used in the combination is 1 to 99 wt %, preferably 20 to 90 wt %, more preferably 50 to 80 wt %, based on the total weight of the combination.

An oxidising agent may be included in the first and/or second components such as a peroxide, such as hydrogen peroxide, zinc peroxide, benzoyl peroxide, potassium peroxide, sodium perborate, potassium perborate, oxone (KHSO$_5$), sodium persulphate, sodium percarbonate, sodium hypochlorite, potassium hypochlorite, ammonium hypochlorite, potassium percarbonate, ammonium percarbonate, ammonium persulphate, potassium persulphate, t-butyl hydroperoxide, magnesium monoperoxyphthalate, sodium peroxide, urea hydrogen peroxide, magnesium peroxide, calcium peroxide, for example or a mixture of any two or more of the foregoing. The oxidising agent may be used in the form of a solution, preferably an aqueous solution, typically in the range 0.1–89.9 wt %, v/v % or mole %, or 0.1 wt % to 70 wt % or v/v %, more typically 1 wt % to 50 wt % or v/v %, based on the total weight or volume of the solution. Typically the amount of oxidising agent used in the second component is 0.01 to 99 wt % or v/v %, preferably 0.1 to 50 wt % or v/v %, more preferably 1 to 30 wt %, even more preferably 2 to 30 wt % or v/v %, based on the total weight of the second component. Typically the oxidising agent is a perborate, persulphate, or percarbonate, or urea hydrogen peroxide. The oxidising agent may be in the form of an aqueous solution typically in the range 1 to 7.9 wt % or v/v and more typically 1 to 5% v/v and even more typically 1 to 3% v/v. Generally when the other components of the combination are in solid form, an oxidising agent in solid form is used (eg in the form of granules, a powder, gel or a tablet) such as a solid form of sodium perborate, potassium perborate, sodium persulphate, sodium percarbonate, potassium percarbonate, ammonium percarbonate, ammonium persulphate, potassijm persulphate, or urea hydrogen peroxide. Ammonium persulphate is especially preferred. Typically the oxidising agent chosen is one for which free chlorine is not produced when the foam is produced. The oxidising typically assists in oxidising any organic matter. Thus, for example, in a toilet bowl the inclusion of oxidising agent has a cleaning action.

The combination may comprise 0.1 to 99 vol %, wt % or mole %, typically 1–99 vol %, wt % or mole %, more typically 1–30 vol %, wt % or mole %, and even more typically 2–10 vol %, wt % or mole %, of further additives such as preservatives, antimicrobial agents, dessicants, perfumes or fragrances, activators, propellants (for aerosols), water softeners, defoamers, or detergent builders. The additives may be included in the first and/or second components, or in the combination when the combination is an integral combination.

Examples of preservatives include glycerine, formalin, sodium benzoate or lower carboxylic acid. Preferably an additive is added to facilatate uptake of the preservative. Typical additives include dimethyl sulphoxide, glyme, diglyme, triglyme, dioxane, pyridine, dimethyl formamide, acetone, tetrahydrofurane, acetonitrile or 1-methyl-2-pyrrolidone.

Examples of antimicrobial agents include antibacterials such as penicillin, amoxycillin, phenol, paraben, chlorobutamol, sorbic acid, sulphur drugs, strongly acidic pH, strongly alkaline pH, 1-phenoxyphenyl-1-triazolylmethyl-carbinols or mixtures thereof.

Examples of perfumes or fragrances include naturally occurring oils and fragrances and synthetic equivalents thereof, for example ambergris, bergamot oil, benzoin oil, castoreum, civet, clove leaf oil, eucalyptus, geranium oil, jasmine absolute, lavender, grapefruit oil or fragrance, citrus fruit oil or fragrance, lemon grass oil, myrrh, musk tonquin, mimosa, rose oil, rosemary oil, or sandalwood oil or synthetic aroma chemicals for example benzyl acetate, citronellol, geraniol, linalool, musk ambrette, or terpinyl acetate. Further examples of perfumes or fragrances are described in "The Perfume Handbook", Nigel Groom, 1st edition, Chapman & Hall 1992, the contents of which are incorporated herein by cross reference.

Examples of activators include copper ions, lead ions, silver ions, zinc ions or other like activators.

The combination can include a desiccant such as silica gel to absorb any moisture and thereby increase shelf life. In the event that the desiccant is silica gel it may be in a form that will not react with the other components of the combination. For example, it may be in the form of beads.

The water softener may be a sequestering agent or chelating agent. Examples of sequestering agents or chelating agents include polyphosphates such as sodium tripolyphosphate or sodium hexametaphosphate; aminocarboxylic acids such as ethylenediaminetetraacetic acid; 1,3-diketones such as acetylacetone; hydroxycarboxylic acids; such as citric acid, tartaric acid or gluconic acid; polyamines such as ethylenediamine; amino alcohols such as triethanolamine, aromatic heterocyclic bases such as dipyridyl; phenols such as salicylaldehyde; Calgor® (sodium hexametaphosphate), Borax® (sodium decahydrate borate), aminophenols such as oxinesulphonic acid; oximes such as dimethylglyoxime; Schiff bases such as disalicylaldehyde 1,2-propylenediimine; tetrapyrroles such as tetraphenylporphin; sulphur compounds such as dimercaptopropanol; synthetic macrocyclic compounds; polymeric compounds or phosphonic acids such as nitrilotrimethylenephosphonic acid.

Generally defoamers control foam formation. Examples of defoamers include fatty alcohols, fatty acid soaps, fatty amides, ethoxylate, or other like defoamers.

Examples of detergent builders include condensed phosphates, sodium sulphate, sodium carbonate, sodium silicate, trisodium nitrilotriacetate, polymaleates, polymethacrylates, polyacrylates or other like detergent builders.

The comination of the invention may also optionally include a colouring agent (eg to colour the foam very light blue) a fragrance or perfume (preferably to provide a grapefruit smell or similar, a methane gas neutraliser or other odorous gas suppressor, leave a slightly alkaline pH in the toilet water to clean the bowl, include a release agent to coat the toilet bowl or other other odour medium container (eg urinal) to stop material sticking thereto, and the base and acid may be optionally separated in the packaging to prevent reaction, thus extending shelf life.

Generally the combination comprises an alkaline effervescent and an acid and at least one foam forming surfactant which together are capable of reacting with water to form a stable foam which floats on water and prevents odours from escaping from the water on which the foam is foamed. The surfactant and (alkaline effervescent and acid) are usually mixed in a weight:[weight], mole:[mole] or volume:[volume] ratio ranging from 50:1 to 1:50, typically the weight:[weight], mole:[mole] or volume:[volume] ratio ranges from 10:1 to 1:1 to 1:10, 5:1 to 1:1 to 1:5, 3:1 to 1:1 to 1:3, 2:1 to 1:1 to 1:2, 1.5:1 to 1:1 to 1:1.5, (surfactant: [alkaline effervescent+acid]). Typically a combination is prepared with more than one surfactant and at least one alkaline effervescent and at least one acidic effervescent. The combination may be in a form wherein the do not react to form a foam until they contact water. For example, the combination may comprises a solid acid, a solid alkaline effervescent, and a solid surfactant in granule, powder, capsule, bead or tablet form for example. The granule or powder may be homogeneous or non homogeneous, coated with a moisture protecting and/or slow substance(s) (eg gelatin or polyvinylalcohol) or uncoated. Some of the powder or granules in the combination may be coated with a moisture protecting substance and other of the powder or granules in the combination may be uncoated (eg uncoated:coated may be in the range from 1:99 to 99:1 wt %, more typically from 20:80 to 80:20 and more typically from 40:60 to 60:40).

When plumbers and drainage maintenance workers uncover sewage or foul water or other hydrous industrial wastes remaining in septic tanks, pipes, grease traps or sullage pits, they are presently required to work under distressing conditions due to very strong odours. In addition the combination of the invention may be administered to a urinal (eg a male urinal trough).

Such odours quite often are due to gases such as hydrogen disulphide, and other sulphide containing gases, methane or sketol, or the like or other odorous gases, which arise via natural occurrence or decay of human, animal and/or plant matter. Present practice is to wear a breathing apparatus to avoid breathing ambient air at the location or replace the foul air at the location via additional ventilation.

The method the subject of the present invention is to dispense sufficient of a combination of the subject invention onto the foul water or other hydrous liquid to form an instant foam covering or odour blanket. The odour blanket forms an air lock between the odour producing liquid and the air above and thereby temporarily prevents unpleasant odours escaping.

The industrial odour blanket method differs from the bathroom cistern method in that the formula in the former could be granulated or in table form, producing two additional advantages:

1) tablets or granules can be distributed to otherwise inaccessible places by being thrown whereas powders can only be scattered in a more limited area.
2) tablets or granules can be produced in differing sizes with different surface areras relative to the quantity of the formula. Smaller relative surface areas retard the reaction and permit the formula to continue reacting for longer after the initial contact with the water or hydrous odour producing medium, thus prolonging the production and persistence of the foam odour blanket.

The industrial odour blanket may have greater perfume concentrations than would be appropriate for domestic bathroom use and could also have greater proportions of an oxidising agent to oxidise odorous gasses in and above the foam blanket.

It is particularly advantageous to apply the method of the invention to form a foam in a toilet bowl or other aqueous odour producing medium, prior to use, typically substantially immediately prior to use. The foam forming components are simply added to or dispensed in the toilet bowl so that a foam is produced without agitating or stirring the water in the toilet bowl.

The volume and concentration of the components may be adjusted to suit water hardness.

According to a third embodiment of this invention there is provided a receptacle for holding and dispensing the combination of the first embodiment comprising:

at least one container capable of holding the first component and the second component; and
means for dispensing the first and second components, the means for dispensing being operatively associated with the container.

According to a fourth embodiment of this invention there is provided a method of deodorising a toilet bowl using a receptacle of the third embodiment having the container including the first component and the second component comprising:

placing the receptacle proximal a toilet bowl or urinal;
dispensing the first and second components into the toilet bowl to form a foam on the water in the toilet bowl or urinal.

The container may have one or more compartments. Typically, it has two compartments, namely a first compartment for holding the first component and a second compartment for holding the second component. As a particular example, it may have two compartments, the first compartment could hold a bicarbonate and a surfactant and the second compartment could hold an acid and a foam forming surfactant. Alternatively there could be a third compartment in addition to the first and second compartments. In the latter case the first compartment could, for example, contain an acid, the second compartment, a bicarbonate and the third compartment a surfactant which forms a foam on contact with water in which carbon dioxide is being generated.

Generally the container is made of plastic, although other materials may be used. For example metals such as aluminium or foil. The container may have a rigid or non rigid shape. The container may be multi-compartmented so that there is one compartment for holding the first component A, and other components such as a foam forming surfactant, a foam promoting agent and a perfume or fragrance, and another compartment for holding the second component B and other components such as an oxidising agent, and the various alternatives shown in Table 1.

The first component and the second component (eg components $A-A_{12}$ and components $B-B_{12}$) may be dispensed separately as aerosols (via either separate aerosol containers or an integral two part container in combination with integral dual aerosol dispensers) to produce a foam. Examples of propellants which may be used in such aerosols include compressed carbon dioxide, compressed hydrocarbons, compressed nitrogen, chlorofluorocarbons, chlorofluorohydrocarbons or other like propellants.

The first component and the second component (eg components $A-A_{12}$ and components $B-B_{12}$) may be dispensed separately (via either separate containers each with their own dispenser or an integral two part container in combination with integral dual dispensers) to produce a foam. Suitable dispensers include any liquid dispenser that can deliver a predetermined amount of liquid such as optic measures, posi-pour measures and Emu measures. The dispensers may also be a straight through pourers such as speed pourers or tubes or the like. The dispenser may be integral with or non integral with the receptacle.

Alternatively, the receptacle may comprise twin chamber bottles that dispense set quantities of liquids from the two chambers when inverted in a further alternative, the receptacle may include dual intermediate internal reservoirs that dispense a measured amount of liiquid, in between two principal reservoirs and a dispensing valve coupled to each intermediate reservoir whereby on actuating the dispensing valves the contents of the intermediate reservoirs are dispensed and the contents of the principal reservoirs are prevented from flowing into the intermediate reservoirs. When the dispensing valves are closed the intermediate reservoirs are refilled automatically from the respective principal reservoirs. In another alternative the receptacle may be one that when touched moves from a stationary equilibrium position into a dispensing position and dispenses predetermined amounts of the first component and the second component (eg components $A-A_{12}$ and components $B-B_{12}$) before returning to the stationary equilibrium position.

In yet another alternative the dispensing means may be a tube which has two ends. One end is located inside one of the compartments whilst the other end is located on the outer surface of the receptacle. The dispensing tube may be formed from flexible materials such as plastic or from non flexible materials such as metal. Generally the dispensing tube is of sufficient length so that the end of the dispensing tube which is on the outer surface of the receptacle acts as securing means for securing the receptacle to the toilet bowl. Alternatively connectors and other tubing may be used to extend the length of the dispensing means in order to secure the receptacle to the toilet bowl.

Generally the actuating means may be a button, a lever, a pedal, a switch or any other similar actuating means. The actuating means may be located anywhere on the receptacle, for example on the upper surface, lower surface or on a side of the receptacle or any other place on or inside the receptacle. The flow of the combination may be caused by a propellant or by displacement of a vacuum within the compartment or by causing disequilibrium to a portion or portions, held in balance, such that they tip and discharge or by similar means. The receptacle may be placed close to the toilet bowl or may be secured to the toilet bowl or any other convenient location. The receptacle may be positioned upright, inverted or placed on its side. The actuating means is initiated by the user prior to defacating, and is not operatively associated with the flushing of the cistern which occurs after defacation.

The combination of the invention in a preferred from as a foil packed metered dose for a toilet bowl of a granulated acid, plus a granulated base plus a powdered surfactant. The contents of the sachet is dropped into the toilet before use and a head of foam rapidly builds up without the need to stir or agitate. The foam typically lasts for 3 or more minutes, typically at least 3 minutes more typically at least 5 minutes (typically 5–20, 5–15 or 5–10 minutes) and provides an airlock seal so the odour of human waste deposited into the toilet by the user does not mix with the surrounding air and odour therefrom is substantially reduced or eliminated.

An advantage of the combination of the invention is that it produces a temporary, airtight foam head which "seals in" odours from solid human waste remaining in the toilet bowl before flushing. Another advantage is that a stable foam is achieved without agitating or stirring the water, achieving an appropriate foam height before equilibrium arrests the production of foam, achieving desirable residual alkaline balance to clean the toilet bowl without toxicity.

A further advantage is that if a lubricating agent is added to the combination, the lubricating agent coats the bowl under the water surface to assist thorough removal of solid waste.

BRIEF DESCRIPTION OF DRAWINGS

A preferred embodiment of the invention is now described with reference to the following drawings in which.

BEST MODE AND OTHER MODES FOR CARRYING OUT THE INVENTION

To prepare a typical foam, the following sets of solutions Part A and part B are prepared separately:

| | wt % Range | Exemplified Component |
|---|---|---|
| Part A | | |
| Alkaline Effervescent | 2–70, typically 10–50 | Sodium Bicarbonate |
| Foam Forming Surfactant | 0.5–99 | Empinin Q70 |
| Foam Forming Surfactant | 0.5–99 | Rhodafac RA |
| Diluent | 1–99.5 | Water |
| Part B | | |
| Acid | 2–50, typically 10–30 | Hydrochloric Acid (30%) |
| Acid | 2–50, typically 10–30 | Citric Acid |
| Foam Forming Surfactant | 0.5–99 | Empilum NP9 |
| Foam Forming Surfactant | 0.5–99 | Rhodafac RA |
| Foam Forming Surfactant | 0.5–99 | Gardiquat 1450 |
| Diluent | 1–99.5 | Water |

Typical formulations for Parts A and B are as follows:

TYPICAL FORMULATIONS

| | wt % | Action |
|---|---|---|
| Part A | | |
| Potassium Bicarbonate | 25 | Alkaline Effervescent |
| Empinin Q70 | 12 | Foam Forming Surfactant |
| Rhodafac RA | 5 | Foam Forming Surfactant |
| Water | 50 | Diluent |
| Part B | | |
| Hydrochloric Acid (30%) | 20 | Acid |
| Citric Acid | 20 | Acid |
| Empilum NP9 | 6 | Foam Forming Surfactant |
| Gardiquat 1450 | 10 | Foam Forming Surfactant |
| Water | 40 | Diluent |

To form a foam, Part A and Part B are mixed together by pouring approximately equal amounts of Parts A and B into water (typically water in a toilet bowl) typically without agitating or stirring the water. The (relative) volumes and/or concentrations of Parts A and B, and the respective components therein, may be adjusted to suit water hardness.

The foam is formed in a toilet bowl before flushing the toilet and typically before the toilet is used.

Figure 1:
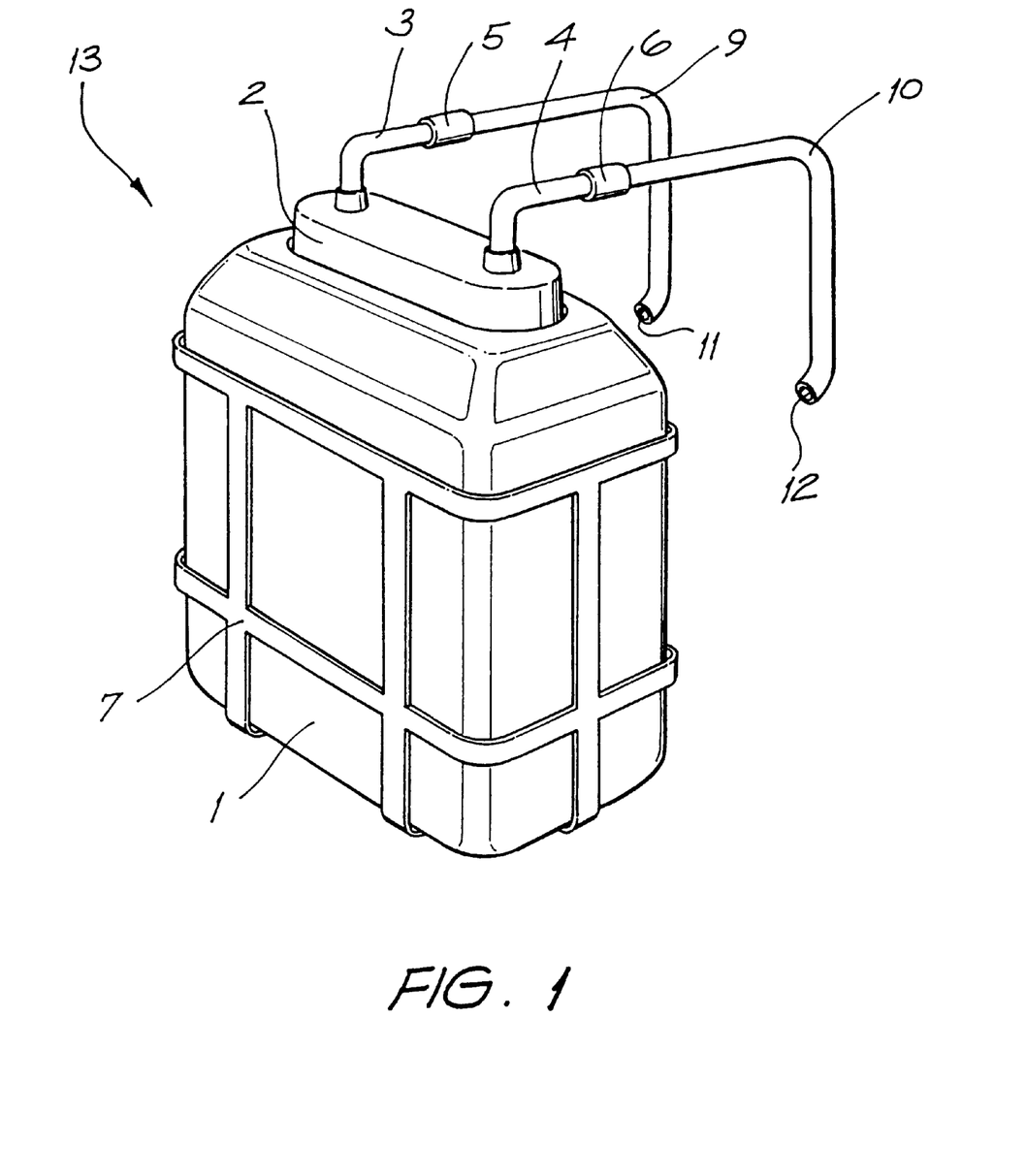
FIG. 1 is a perspective view of a receptacle of the invention.

Referring to FIG. 1, a receptacle 13 comprises a container 1, an actuating means 2 and two dispensing tubes 3, 4. The container 1 is preferably made of plastic and has two compartments which are separated by a divider. Typically one compartment contains a surfactant and an alkaline effervescent (Part A solution) and the other compartment contains a surfactant and an acid (Part B solution).

The actuating means 2 is typically a pressure button which when depressed, compresses the air in container 1, thereby cause the Part A solution of the combination to travel through dispensing tube 3 and the Part B solution of the combination to travel through dispensing tube 4.

Figure 2:
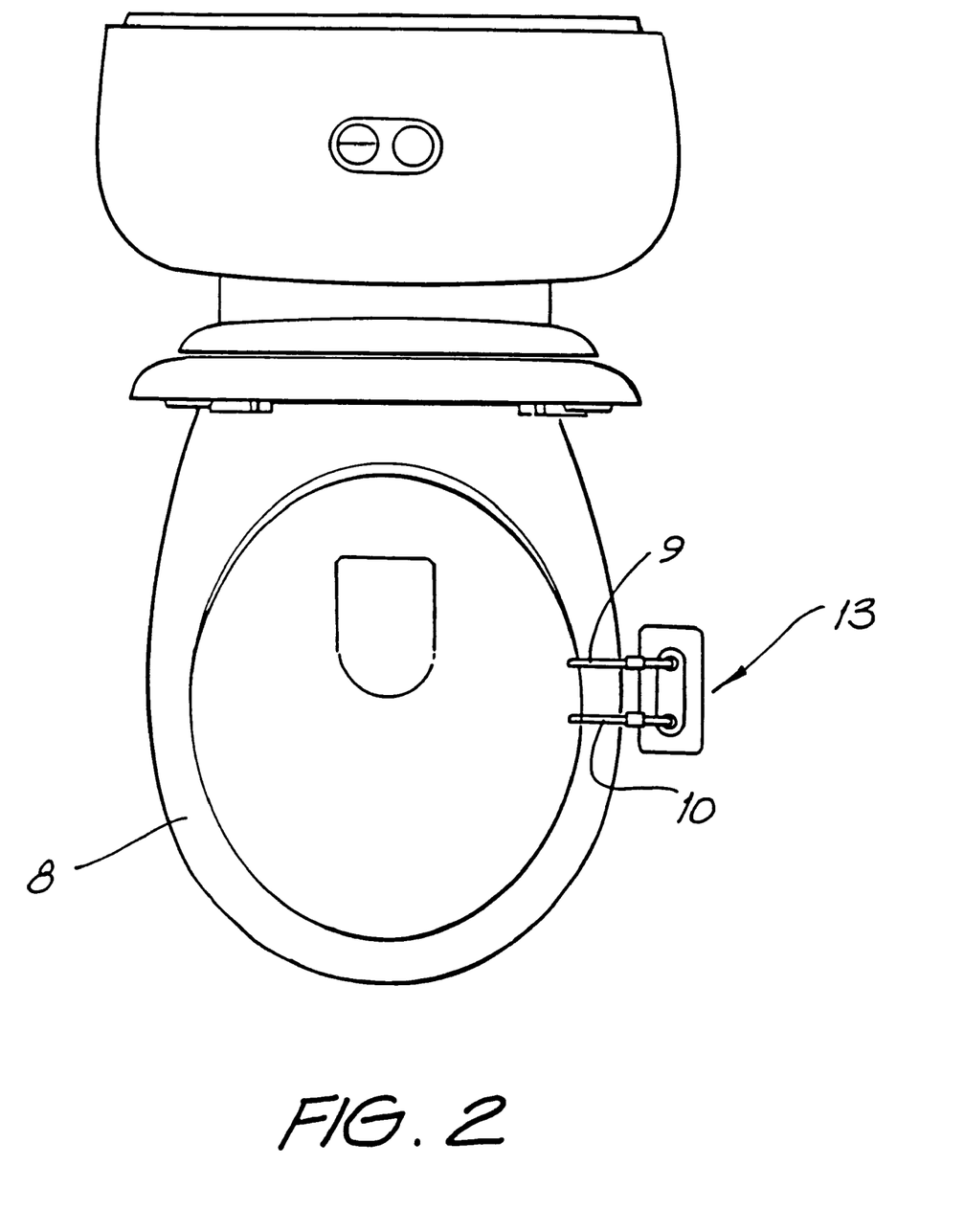
FIG. 2 is a top plan view of a toilet bowl with the receptacle of FIG. 1 attached to the rim of the toilet bowl.

The dispensing tubes 3, 4 are typically made of plastic. A nipple 5 is located on dispensing tube 3 and a nipple 6 is located on dispensing tube 4. The nipples 5, 6 are located at the ends of the dispensing tubes 3,4 closest to the actuating means 2. The nipple 5 connects tube 9 to dispensing tube 3 and nipple 6 connects tube 10 to dispensing tube 4. The tubes 9, 10 are shaped so that they conveniently rest on the rim of the toilet bowl 8 and fold around the rim. In this position, openings 11, 12 face into the toilet bowl 8. This is illustrated in FIG. 2.

The receptacle 13 may be placed in a basket 7 as illustrated in FIG. 1 to anchor the receptacle 13. The tubes 9, 10 secure the receptacle 13 by clamping around the toilet bowl 8 with openings 11, 12 facing inside the toilet bowl 8.

To install a receptacle 13, one compartment of a two part compartment container 1 is filled with a Part A solution of the combination and the other compartment of the two part compartment container 1 is filled with a Part B solution of the combination. The actuating means 2 is then placed onto the container 1. The dispensing tubes 3, 4 may be placed on to the actuating means 2 before the actuating means 2 is placed on the container 1 or after the actuating means 2 is placed on the container 1. Similarly nipples 5, 6 and tubes 9, 10 may be placed on dispensing tubes 3, 4 either before or after actuating means 2 is placed on container 1.

When the receptacle 13 is assembled, container 1 is placed into a basket 7. The receptacle 13 is then placed onto the side of toilet bowl 8 by placing the tubes 9, 10 over the rim of the toilet bowl 8 so that openings 11, 12 are facing into toilet bowl 8. In this position, the receptacle 13 is left outside the toilet bowl 8. The basket 7 allows receptacle 13 to be left on the floor beside toilet bowl 8 or to be attached to some point on the toilet hidden from view or simply hung off the side of toilet bowl 8 or suspended inside the cistern tank. In FIG. 1 receptacle 13 is drawn with the actuating means 2 on the upper portion of container 1. FIG. 1 also shows container 1 sitting in basket 7 with the upper portion of container 1 at the top of the drawing. Alternatively the actuating means 2 may be located on the lower portion of container 1 and container 1 may be inverted in basket 7.

To use the receptacle 13 of the invention, a person wishing to defecate, depresses the actuating means 2 before defecation. This action causes the components to be dispensed from the dispensing tubes 3, 4 and pass through the openings 11, 12. After the components leave the openings 11, 12, the components mix with water in the toilet bowl 8 to form a foam. The resultant foam acts as a barrier to trap any odours.

An alternative combination of the invention is one of, for example, a one (or two) part homogeneous powder or granule combination I–VII below.

COMBINATION I

| | |
|---|---|
| Acid optionally anhydrous, solid and in granulated or powdered form: | 5–90 wt % or mole % |
| Carbonate or bicarbonate optionally anhydrous solid and in granulated or powdered form: | 5–90 wt % or mole % |
| Surfactant, solid and in granulated or powdered form: | 0.1–90 wt % or mole % |

COMBINATION II

| | |
|---|---|
| Acid optionally anhydrous, solid and in granulated or powdered form: | 5–90 wt % or mole % |
| Carbonate or bicarbonate optionally anhydrous, solid and in granulated or powdered form: | 5–90 wt % or mole % |
| Surfactant, solid and in granulated or powdered form: | 0.1–89.9 wt % or mole % |
| Oxidising agent, solid and in granulated or powdered form: | 0.1–89.9 wt % or mole % |

COMBINATION III

| | |
|---|---|
| Acid optionally anhydrous, solid and in granulated or powdered form: | 5–90 wt % or mole % |

| | |
|---|---|
| Carbonate or bicarbonate optionally anhydrous, solid and in granulated or powdered form: | 5–90 wt % or mole % |
| Surfactant, solid and in granulated or powdered form: | 0.1–89.9 wt % or mole % |
| Foam stabilising agent, solid and in granulated or powdered form: | 0.1–89.9 wt % or mole % |
| COMBINATION IV | |
| Acid optionally anhydrous, solid and in granulated or powdered form: | 5–90 wt % or mole % |
| Carbonate or bicarbonate optionally anhydrous, solid and in granulated or powdered form: | 5–90 wt % or mole % |
| Surfactant, solid and in granulated or powdered form: | 0.1–89.9 wt. % or mole % |
| Foam stabilising agent, solid and in granulated or powdered form: | 0.1–89.9 wt % or mole % |
| Oxidising agent, solid and in granulated or powdered form: | 0.1–89.9 wt % or mole % |
| COMBINATION V | |
| Acid optionally anhydrous, solid and in granulated or powdered form: | 5–90 wt % or mole % |
| Carbonate or bicarbonate optionally anhydrous, solid and in granulated or powdered form: | 5–90 wt % or mole % |
| Surfactant, solid and in granulated or powdered form: | 0.1–89.7 wt % or mole % |
| Foam stabilising agent, solid and in granulated or powdered form: | 0.1–89.7 wt % or mole % |
| Oxidising agent, solid and in granulated or powdered form: | 0.1–89.7 wt % or mole % |
| Perfume and Other additives, solid and in granulated or powdered form | 0.1–89.7 wt % or mole % |
| COMBINATION VI | |
| Acid, solid and in granulated or powdered form: | 5–90 wt % or mole % |
| Carbonate or bicarbonate, solid and in granulated or powdered form: | 5–90 wt % or mole % |
| Surfactant, solid and in granulated or powdered form: | 0.1–90 wt % or mole % |
| COMBINATION VII | |
| an acid, optionally anhydrous, selected from the group consisting of citric acid, tartaric acid, boric acid, saccharic acid, tartronic acid, oxalic acid, succinic acid, tartaric acid, salicyclic acid, adipic acid, and ascorbic acid, | 5–90 wt % or mole % |
| an alkaline effervescent compound, optionally anhydrous, selected from the group consisting of sodium hydrogen carbonate, potassium bicarbonate and ammonium bicarbonate, | 5–90 wt % or mole % |
| a surfactant selected from the group consisting of sodium methyl oleoyl taurate, sodium lauryl sulphate and sodium alkyl benzene sulphonate, | 0.1–89.8 wt % or mole % |
| a foam promoting agent selected from the group consisting of xanthan gum, sodium alginate, potassium alginate and ammonium alginate, and | 0.1–89.8 wt % or mole % |
| optionally an oxidising agent selected from the group consisting of sodium perborate, potassium perborate, oxone (KHSO$_5$), sodium persulphate, sodium percarbonate, sodium hypochlorite, potassium hypochlorite, ammonium hypochlorite, potassium percarbonate, ammonium percarbonate, ammonium persulphate, potassium persulphate, and urea hydrogen peroxide. | 0.1–89.7 wt % or mole % |

Enough of the granules or powder are typically packaged in an air tight package (eg a moisture tight satchel such as a plastic satchel or aluminium satchel, a blister pack, a moisture tight bag such as a heat sealed plastic bag, a sealable bottle or jar such as a screw top plastic bottle or jar) so as to form the desired amount of foam for the intended use. Typically combinations I–VII may include other additives such as perfumes and fragrances, a desiccant, etc. Thus, for example, if the intended use was to cover the water in an Australian, European, Japanese or American style toilet, for example, or a sewer, waste or drainage pipe or trap or aqueous industrial waste, for example, then the amount of powder in each satchel would be enough to provide a sufficient covering of foam when the contents of the satchel was emptied into such a toilet, sewer, waste or drainage pipe or trap, containing water (eg enough to provide foam coverage of the water in the range of 0.15–25 cm, 1–20 cm, 1–15 cm, 1–10 cm, 1–8 cm, 1–5 cm, 1–3 cm, 2–20 cm, 2–15 cm, 2–10 cm, 2–8 cm, 2–5 cm, 2–3 cm, more typically 2–6 cm foam coverage over the water). Alternatively, the granules or powder are packaged in a container such as a screw top plastic bottle and the user can dispense enough the granules or powder to obtain the required head of foam.

In use just prior to defacation (eg 5 seconds–3 minutes) the user simply dispenses powder or granules of one of combinations I–VII into a toilet bowl sufficient to form a desired head of foam with external agitation of the water in the toilet bowl. A sufficient head of foam is one that substantially blocks odorous smells emanating from the water and is typically 1–5 cm). As a result of the reactions of the components of the combination on contact with water in the a layer of foam forms on top of the toilet water soon after the powder or granules contact the water in the bowl.

EXAMPLES

Other examples of formulations are:

| | Formula 1 wt % | Formula 2 wt % | Formula 3 wt % | Formula 4 wt % | Formula 5 wt % | Action |
|---|---|---|---|---|---|---|
| Part A | | | | | | |
| Sodium Bicarbonate | 20 | 25 | 25 | 30 | 30 | Alkaline Effervescent |
| Empinin Q70 | 10 | 20 | 10 | 5 | 15 | Foam Forming Surfactant |
| Rhodafac RA | 10 | 5 | 5 | 5 | 5 | Foam Forming Surfactant |
| Water | 60 | 50 | 60 | 60 | 50 | Diluent |

-continued

|  | Formula 1 wt % | Formula 2 wt % | Formula 3 wt % | Formula 4 wt % | Formula 5 wt % | Action |
|---|---|---|---|---|---|---|
| Part B |  |  |  |  |  |  |
| Hydrochloric Acid (30%) | 10 | 20 | 15 | 10 | — | Acid |
| Citric Acid | 40 | 20 | 15 | 40 | 40 | Acid |
| Rhodafac RA 600 | 5 | — | — | — | — | Foam Forming Surfactant |
| Empilum NP9 | 10 | 10 | 20 | 5 | 10 | Foam Forming Surfactant |
| Gardiquat 1450 | 10 | 10 | 20 | 5 | 10 | Foam Forming Surfactant |
| Water | 25 | 40 | 30 | 40 | 40 | Diluent |

Sodium bicarbonate may be replaced with or used in addition to potassium carbonate or potassium bicarbonate for example and sulphuric acid may be replaced with or used in addition to hydrochloric acid, citric acid or ascorbic acid, for example. One or all of the surfactants may be replaced by or used in addition to Rhodafac RA, G9 A6 Teric, N9 Teric, N4 Teric or mixtures thereof, for example.

Examples of the Reactions of Table 1 are based on the liberation of carbon dioxide gas. The equations are as follows:

$$CO_3^{2-} + 2H^+ \rightarrow H_2CO_3 \rightarrow H_2O + CO_2 \circ$$

carbonate+hydrogen ion→carbonic acid→water+carbon dioxide $$HCO_3^- + H^+ \rightarrow H_2CO_3 \rightarrow H_2O + CO_2 \circ$$

bicarbonate+hydrogen ion→carbonic acid→water+carbon dioxide

The following examples illustrate various reactions of Table 1 and combinations of the invention.

EXAMPLE 1

Soap flakes (3 parts) in water+sodium cholate (1 part) in water→foam

EXAMPLE 2

Sodium bicarbonate (250 parts)+citric acid (125 parts)+water→carbon dioxide

Carbon dioxide+Calgon (25 parts)+water→foam

EXAMPLE 3

Sodium carbonate (15 parts)+sodium bicarbonate (10 parts)+sodium acid sulphate (1 parts)+water→carbon dioxide Carbon dioxide+Calgon (24 parts)+water→foam

EXAMPLE 4

Sodium bicarbonate (12 parts)+tartaric acid (7 parts)+water→carbon dioxide

Carbon dioxide+Borax (2 parts)+sodium lauryl sulphate (20 parts)+water→foam

EXAMPLE 5

A carbon dioxide generator

Carbon dioxide+soap flakes (3 parts) in water+sodium cholate (1 part) in water→foam

EXAMPLE 6

A carbon dioxide generator

Carbon dioxide+Castile soap (3 parts) in water+glycerine (1 part) in water→foam

EXAMPLE 7

A carbon dioxide generator

Carbon dioxide+soap (15 parts)+gum arabic (2 parts)+glycerol (6 parts)+dye (0.3 parts)+water (76.7 parts)→foam

EXAMPLE 8

Sodium carbonate (300 parts)+tartaric acid (225 parts)+water→carbon dioxide

Carbon dioxide+Borax (400 parts)+Pinus Montana Needle Oil (15 parts)+Pine Needle Oil (15 parts)+sodium sulphate (200 parts)+lactose (50 parts)+talcum (25 parts)+fluorescein (6–12 parts)+water→foam

EXAMPLE 9

A carbon dioxide generator

Carbon dioxide+soap flakes (3 parts) in water+sodium cholate (1 part) in water→foam

EXAMPLE 10

This is an example of producing a liquid foam without using carbon dioxide or some other gas.

Aluminium sulphate-saturated solution+sodium bicarbonate (5–7 parts)+water (to 100 parts)+stabiliser (4–6 parts)→foam.

The stabiliser may be licorice extract, lignum, egg albumin, glue or dry hydrolysed protein.

EXAMPLE 11

The following formula, especially in pellet, granular or powder foam, was found to provide an excellent stable foam (stable for at least 10 minutes at a thickness of about 2 cm) in an Australian toilet (25 grams was found to be adequate in an Australian toilet, if used in an American or European toilet that have wider bowls then between 35–150 grams, typically 50–80 grams, of the following formula is typically used):

| | |
|---|---|
| Citric acid anhydrous: | 16 g |
| Sodium hydrogen carbonate anhydrous: | 21 g |
| *Geropon T-77 (Sodium Methyl Oleoyl Taurate): | 3 g |
| #Xanthan gum (Keltrol-F): | 1 g |
| *Sodium percarbonate: | 1 g |

Other types of surfactants, eg.: Decol BD/80 and sodium lauryl sulphate, may be substituted or used in combination with one another or in combination with Geropon T-77.
Other types of foam stabilising agents, e.g.: Sodium alginate, ammonium alginate, and potassium alginate, may be substituted or used in combination with one another or in combination with xanthan gum.
*Other types of peroxide producing agents, eg.; Sodium persulphate, ammonium persulphate, potassium persulphate, and oxone may be substituted or used in combination with one another or in combination with sodium percarbonate.

EXAMPLE 12

The ideal product for domestic use would be a single dose per use be added to a toilet bowl before defecation, that creates a dense foam of sufficient foam height and stability to prevent odour release. This may be as a liquid, tablet, powder, granule, capsule, pellet or similar. Other possibilities include a two or more part system which was premixed immediately prior to addition or added simultaneously or in sequence.

Addition could be from a unit dose container such as a sachet or blister pack or from a multi dose container with or without a device to dispense a predetermined quantity.

The invention would normally be expected to contain at least 2 components.

(a) a suitable detergent, preferably biodegradable, non-toxic and ecologically sound;
(b) a means of generating agitation to produce foam, either chemically or mechanically.

It may also contain other components for:

(c) sensitising and disinfecting—eg. quaternary ammonium compounds, oxidising agent.
(d) odour masking, odour absorbing, odour adsorbing or odour modifying—eg perfumes, macrocyclic compounds.
(e) colouring agents (preferably biodegradable and/or naturally derived)—eg. Brillant Blue FCF.
(f) foaming stabilising.

EXPERIMENTAL TESTING

It is especially desirable to use an acid and a carbonate that have been processed and packaged under low humidity conditions. It is especially desirable that the acid is sufficiently strongly acidic and the carbonate sufficiently water solution to produce an instant effervescent agitation to produce a stable foam. Large tablets with small surface area have the disadvantage that they must disintegrate first before the reaction can occur. Multiple small tablets, of for example 100 mg or less are more desirable as they can potentially produce strong effervescence in the toilet and normally enough to provide the foam height required. Liquids were less effective due to the solubility limits of the carbonate/bicarbonate and the need to add large quantities per use to obtain a sufficient agitation.

Especially suitable combinations were found to be powder or granule with high concentrations of effervescent ingredients and small quantities of detergents. A suitable formula was found to be

| | |
|---|---|
| Citric Acid anhydrous | 16 g |
| Sodium Bicarbonate | 21 g |
| Sodium Lauryl Sulphate | 3 g |

These ingredients were milled and mixed and found to produce instantaneously a dense white foam in the toilet of about 1–2 cm.

Further tests were carried out using other surfactants with the following results.

| Test No. | Sodium Bicarb. | Citric Acid Anh. | Detergent | Foam Density | Foam Stability | Foam Height (cm) |
|---|---|---|---|---|---|---|
| 1 | 16 g | 21 g | 5 g Polysorbate 20 | Dense | Stable | 3–4 |
| 2 | 16 g | 21 g | 5 g Polysorbate 60 | Dense | Stable | 3–4 |
| 3 | 16 g | 21 g | 5 g Coconut Diethanolamide | Very Dense | Stable | 3–4 |
| 4 | 16 g | 21 g | 5 g Ethoxylated lauryl alcohol (8 moles EO) | Very Dense | Stable | 3–4 |
| 5 | 16 g | 21 g | 5 g Sorbitan Monoleate | Very Dense | Stable | 3–4 |
| 6 | 16 g | 21 g | 5 g Teric BLS | Very Dense | Stable | 3–4 |
| 7 | 16 g | 21 g | 5 g Teric 9A8 | Very Dense | Stable | 3–4 |
| 8 | 16 g | 21 g | 5 g PEG 75 Lanolin | Very Dense | Stable | 3–4 |
| 9 | 16 g | 21 g | 5 g Benzethonium Chloride | Very Dense | Stable | 3–4 |
| 10 | 16 g | 21 g | 5 g Soap Chips | Medium | Moderate | 2–3 |
| 11 | 16 g | 21 g | 5 g Sodium Lauryl Sulphonate | Dense | Stable | 3 |
| 12 | 8.6 g | 11.4 g | 2 g Coconut Diethanolamide | Very Dense | Stable | 2–3 |
| 13 | 8.6 g | 11.4 g | 1 g Polysorbate | Very Dense | Stable | 1–2 |
| 14 | 8.6 g | 11.4 g | 0.5 g Polysorbate 60 | Dense | Stable | 1–2 |
| 15 | 8.6 g | 11.4 g | 0.1 g Polysorbate 20 | Dense | Stable | 1–2 |
| 16 | 8.6 g | 11.4 g | 2.5 g of 1.5% Polysorbate 20 adsorbed on Sodium Bicarbonate | Medium | Just stable | 1–2 |
| 17 | 6.5 g | 8.5 g | 2.5 g of 1.5% Polysorbate 20 adsorbed on Sodium Bicarbonate | Medium | Just stable | 1–2 |
| 18 | 4.3 g | 5.7 g | 2.5 g of 1.5% Polysorbate 20 adsorbed on Sodium Bicarbonate | Medium | Just stable | 1–2 |
| 19 | 2.6 g | 3.4 g | 2.5 g of 1.5% Polysorbate 20 adsorbed on Sodium Bicarbonate | Coarse | Just stable | 1–2 |
| 20 | 8.6 g | 11.4 g | 2 g Polysorbate 20 + 0.5 g Tea Tree Oil | Very Dense | Stable | 3–4 |

CONCLUSIONS

A foam height of 1–2 cm or more was found satisfactory as long as it was dense and stable. The advent of high fibre diets producing less dense floating faeces (rather than sinking faeces) suggest that this would be a desirable foam height for the product.

(a) Dosage Form: Granules, powder or small tablets (with high surface area) would produce the best results. The effervescence may be generated from the reaction of an acid on a carbonate or bicarbonate. Stoichiometric quantities of each are typically used as this produces the largest amount of effervescence (agitation) for the smallest quantity. A slight excess of one or the other ingredient (eg 0.01–10 mole %) may be used to control the pH of the end product so that it is compatible with the requirements of the sewerage system and authorities.

(b) The acid may be organic or inorganic, but use in powders, tablets or granules requires a "solid" acid such as citric or tartaric.

(c) The carbonate will normally be inorganic such as sodium or potassium carbonate or bicarbonate.

(d) Detergent—may be anionic, cationic, non-ionic or amphoteric. High foaming detergents were found to be best such as sodium lauryl sulphate. Polysorbate 20 (Tween 20), Coconut diethanolamide or Ethoxylated fatty alcohols (eg. Tetric 12A8 and 12A12). Final selection would depend on long term stability in the chosen packaging system.

Detergents and surfactants are usually supplied in the pure form or in aqueous solutions. All high foaming detergents tested in the pure form were found satisfactory.

Liquid or paste surfactants could be absorbed onto a solid support (eg. silicon dioxide, salt or one of the effervescent components) and still work effectively. The finer the particle size of the solid support, the greater the surface area and the more effective the effervescence and foaming. Surfactants containing water could be adsorbed and then dried and still work effectively.

(e) Other components such as perfumes, germicides, encapsulates, colours or other additives may be successfully incorporated into the formula.

INDUSTRIAL APPLICABILITY

A combination capable of forming an odour barrier can be readily utilised in the hospitality industry, in the plumbing industry, in the home, in hospitals, in public conveniences to provide a temporary, airtight foam head which "seals in" odours from solid human waste remaining in the toilet bowl before flushing. Similar industrial applications may exist whenever odiferous materials are stored and there is a need to temporarily arrest the mixing of odours with the surrounding air, such as in the service of waste pipes or sewers.

I claim:

1. A combination capable of forming an odour barrier comprising a stable foam, the combination comprising:
  (i) a first component comprising an alkaline effervescent compound in solid form,
  (ii) a second component comprising an acid in solid form,
  (iii) an oxidising agent in solid form, and
  (iv) an activator
  wherein at least one of the first component and second component comprises a stable foam-forming surfactant in solid form,
  the first component reacts with the second component to form a stable foam odour barrier which traps/blocks odours emanating from an aqueous based medium,
  together with a multi-compartmented air-tight and moisture-tight container,
  wherein the first component and second component of the combination are packaged in the multi-compartmented air-tight and moisture-tight container, thereby separating the base and acid components in the packaging to prevent reaction, until combination is required to form an odour barrier by addition to an aqueous medium.

2. The combination of claim 1 wherein the first component comprises an alkaline effervescent compound selected from the group consisting of sodium bicarbonate, potassium carbonate, ammonium bicarbonate, ammonium carbonate, sodium carbonate, potassium bicarbonate and any mixture thereof.

3. The combination of claim 1 wherein the second component comprises an acid selected from the group consisting of citric acid, tartaric acid, boric acid, stearic acid, palmitic acid, glucuronic acid, alpha-hydroxybutyric acid, alpha-hydroxyisobutyric acid, mandelic acid, beta-phenyllactic acid, beta-phenylpyruvic acid, saccharic acid, tartronic acid, betahydroxybutyric acid, malic acid, citramalic acid, mucic acid, glycolic acid, hydroxyglutaric acid, lactic acid, catechol acid, oxalic acid, succinic acid, tartaric acid, salicylic acid, adipic acid, ascorbic acid and any mixture thereof.

4. The combination of claim 1 wherein the foam forming surfactant is selected from the group consisting of an anionic, cationic, amphoteric and nonionic surfactant.

5. The combination of claim 1, wherein the foam forming surfactant is selected from the group consisting of water-soluble soaps; water-soluble synthetic surface active compounds; unsubstituted or substituted ammonium salts of $C_{10}$–$C_{20}$-fatty acids; alkylarylsulphonates; sulphonated benzimidazole derivatives; fatty alcohol sulphates; fatty alcohol sulphonates; polyglycol ether derivatives of aliphatic alcohols having approximately 3 to 30 glycol ether groups and approximately 8 to 20 carbon atoms in the aliphatic hydrocarbon moiety; polyglycol ether derivatives of cycloaliphatic alcohols having approximately 3 to 30 glycol ether groups and approximately 8 to 20 carbon atoms in the aliphatic hydrocarbon moiety; saturated or unsaturated fatty acids and alkylphenols having approximately 6 to 18 carbon atoms in the alkyl moiety of the alkylphenols; water-soluble adducts of polyethylene oxide and a polypropylene glycol compound selected from the group consisting of ethylenediaminopolypropylene glycol, polypropylene glycol, and alkylpolypropylene glycol, wherein the polypropylene glycol having approximately 1 to 10 carbon atoms in the alkyl chain, having approximately 20 to 250 ethylene glycol ether groups and approximately 10 to 100 propylene glycol ether groups in the usual ratio of 1 to 5 ethylene glycol moiety; propylene glycol moiety; fatty acid esters of polyoxyethylene sorbitan; quaternary ammonium salts in the form of halides; quaternary ammonium salts in the form of methylsulphates; quaternary ammonium salts in the form of ethylsulphates; aminocarboxylic acids and salts thereof; aminosulphonic acids and salts thereof; nonylphenol ethoxylates; phosphated alkyl ethoxylates; sodium fatty alcohol triethoxysulfates; fatty alcohol ethoxylates; coconut monoethanol amides; coconut diethanolamides; coconut isopropanolamides; alkylbenzyldimethyl ammonium chlorides; sodium alkyl benzene sulfonates; soap; sodium lauryl sulphate; sodium alkyl benzene sulphonate sodium cholate; sodium methyl oleoyl taurate and any mixture thereof.

6. The combination of claim 1 wherein the combination further includes a foam promoting agent.

7. The combination of claim 6 wherein the foam promoting agent is selected from the group consisting of methyl isobutyl carbinol, 4-methyl-2-pentanol, poly(propylene glycol) methyl ethers, glycerol, cresylic acid, soaps, proteins, extract of licorice root, extract of fatty acids, extract of sulphite liquors, starch, sodium carboxymethyl cellulose, methocel, carboxy vinyl polymers, sodium alginate, potassium alginate, ammonium alginate, xanthan gum, magnesium aluminum silicates, methyl cellulose, natural gums, gum arabic, clays, soap gels, lipophilic fatty acid esters, alum cocamide, cocamidoethyl betaine, cocamidopropyl betaine, cocamidopropyl hydroxysultaine, coco-amphodipropionic acid, coco-betaine, coco/oleamidopropyl betaine, coco-sultaine, cocoyl hydroxyethyl imidazoline, polyvinylpyrrolidone, polyox, cetyl betaine, decyl betaine, DEA-cocamphodipropionate, DEA-lauraminopropionate, disodium isostearyl sulphosuccinate, isopropyl stearate, lauramide, lauramidopropyl betaine, lauryl betaine, lauryl sultaine, myristamidopropyl betaine, myristaminopropionic acid, myristyl betaine, oleamidopropyl betaine, oleamidopropyl hydroxysultaine, oleyl betaine, palmamidopropyl betaine, palmitamidopropyl betaine, PEG-3 lauramide, PEG-S lauramide, PEG-6 lauramide, sodium cocoamphoacetate, sodium cocoamphopropionate, sodium lauraminopropionate, sodium lauroamphopropionate, sodium lauroyl sarcosinate, sodium myristoamphoacetate, sodium myristoyl sarcosinate, TEA-hydrogenated tallow glutamate, TEA-lauraminopropionate, TEA myristaminopropionate or undecylenamidopropylamine oxide, alumina gel, and any mixture thereof.

8. The combination of claim 1, wherein the oxidising agent is selected from the group consisting of a peroxide, zinc peroxide, benzoyl peroxide, potassium peroxide, sodium perborate, potassium perborate, oxone of the formula, sodium persulphate, sodium percarbonate, sodium hypochlorite, potassium hypochlorite, ammonium hypochlorite, potassium percarbonate, ammonium percarbonate, ammonium persulphate, potassium persulphate, magnesium monoperoxyphthalate, sodium peroxide, urea hydrogen peroxide, magnesium peroxide, calcium peroxide, and any mixture thereof.

9. The combination of claim 1 wherein the combination comprises a combination selected from the group consisting of

| COMBINATION I | |
|---|---|
| Acid, optionally anhydrous, solid and in granulated or powdered form: | 5–90 wt % or mole % |
| Carbonate or bicarbonate, optionally anhydrous, solid and in granulated or powdered form: | 5–90 wt % or mole % |
| Surfactant, solid and in granulated or powdered form. | 0.1–89.9 wt % or mole % |
| Oxidising agent, solid and in granulated or powdered form: | 0.1–89.9 wt % or mole % |
| COMBINATION II | |
| Acid, optionally anhydrous, solid and in granulated or powdered form; | 5–90 wt % or mole % |
| Carbonate or bicarbonate, optionally anhydrous, solid and in granulated or powdered form: | 5–90 wt % or mole % |
| Surfactant, solid and in granulated or powdered form: | 0.1–89.9 wt % or mole % |
| Foam promoting agent, solid and in granulated or powdered form: | 0.1–89.9 wt % or mole % |
| Oxidising agent, solid and in granulated or powdered form: | 0.1–89.9 wt % or mole % |
| COMBINATION III | |
| Acid, optionally anhydrous, solid and in granulated or powdered form: | 5–90 wt % or mole % |
| Carbonate or bicarbonate, optionally anhydrous, solid and in granulated or powdered form: | 5–90 wt % or mole % |
| Surfactant, solid and in granulated or powdered form: | 0.1–89.7 wt % or mole % |
| Foam promoting agent, solid and in granulated or powdered form: | 0.1–89.7 wt % or mole % |
| Oxidising agent, solid and in granulated or powdered form: | 0.1–89.7 wt % or mole % |
| Perfume and Other additives, solid and in granulated or powdered form | 0.1–89.7 wt % or mole % |

10. The combination of claim 1 wherein the combination comprises:
(i) 5–90 wt % or mole % of an acid, optionally anhydrous, selected from the group consisting of citric acid, tartaric acid, boric acid, saccharic acid, tartronic acid, oxalic acid, succinic acid, tartaric acid, salicylic acid, adipic acid, and ascorbic acid,
(ii) 5–90 wt % or mole % of an alkaline effervescent compound, optionally anhydrous, selected from the group consisting of sodium hydrogen carbonate, potassium bicarbonate, and ammonium bicarbonate,
(iii) 0.1–89.8 wt % or mole % of a surfactant selected from the group consisting of sodium methyl oleoyl taurate, sodium lauryl sulphate and sodium alkyl benzene sulphonate,
(iv) 0.1–89.8 wt % or mole % of a foam promoting agent selected from the group consisting of xanthan gum, sodium alginate, potassium alginate and ammonium alginate,
(v) 0.1–89.7 wt % or mole % of an oxidising agent selected from the group consisting of sodium perborate, potassium perborate, oxone of the formula, sodium persulphate, sodium percarbonate, sodium hypochlorite, potassium hypochlorite, ammonium hypochlorite, potassium percarbonate, ammonium percarbonate, ammonium persulphate, potassium persulphate, and urea hydrogen peroxide 0.1–89.7 wt % or mole %.

11. A method of trapping/blocking odors emanating from an aqueous based medium comprising contacting the aqueous based medium with a combination capable of forming an odour barrier comprising a stable foam, the combination comprising:
(i) a first component comprising an alkaline effervescent compound in solid form,
(ii) a second component comprising an acid in solid form,
(iii) an oxidising agent in solid form, and
(iv) an activator
wherein at least one of the first component and second component comprises a stable foam-forming surfactant in solid form,
the first component reacts with the second component to form a stable foam odour barrier which traps/blocks odours emanating from an aqueous based medium,
together with a multi-compartmented air-tight and moisture-tight container,
wherein the first component and second component of the combination are packaged in the multi-compartmented air-tight and moisture-tight container, thereby separating the base and acid components in the packaging to prevent reaction, until combination is required to form an odour barrier by addition to an aqueous medium.

12. The method of claim 11 wherein the first component comprises an alkaline effervescent compound selected from the group consisting of sodium bicarbonate, potassium carbonate, ammonium bicarbonate, ammonium carbonate, sodium carbonate, potassium bicarbonate and any mixture thereof.

13. The method of claim 11 wherein the second component comprises an acid selected from the group consisting of citric acid, tartaric acid, hydrochloric acid, sulphuric acid, nitric acid, oleic acid, boric acid, stearic acid, palmitic acid, glucuronic acid, alphahydroxybutyric acid, alpha-hydroxyisobutyric acid, mandelic acid, pyruvic acid, beta-phenyllactic acid, beta-phenylpyruvic acid, saccharic acid, tartronic acid, betahydroxybutyric acid, malic acid, citramalic acid, mucic acid, glycolic acid, hydroxyglutaric acid, lactic acid, catechol acid, oxalic acid, succinic acid, tartaric acid, salicylic acid, adipic acid, ascorbic acid and any mixture thereof.

14. The method of claim 11 wherein the foam forming surfactant is selected from the group consisting of an anionic, cationic, amphoteric and nonionic surfactant.

15. The method of claim 11 wherein the foam forming surfactant is selected from the group consisting of water-soluble soaps; water-soluble synthetic surface active compounds; unsubstituted or substituted ammonium salts of $C_{10}$–$C_9$-fatty acids; alkylarylsulphonates; sulphonated benzimidazole derivatives; fatty alcohol sulphates; fatty alcohol sulphonates; polyglycol ether derivative of aliphatic alcohols having approximately 3 to 30 glycol ether groups and approximately 8 to 20-carbon atoms in the aliphatic hydrocarbon moiety; polyglycol ether derivatives of cycloaliphatic alcohols having approximately 3 to 30 glycol ether groups and approximately 8 to 20 carbon atoms in the aliphatic hydrocarbon moiety; saturated or unsaturated fatty acids and alkylphenols having approximately 6 to 18 carbon atoms in the alkyl moiety of the alkylphenols; water-soluble adducts of polyethylene oxide and a polypropylene glycol compound selected from the group consisting of ethylenediaminopolypropylene glycol, polypropylene glycol, and alkylpolypropylene glycol, wherein the polypropylene glycol compound having approximately 1 to 10 carbon atoms in the alkyl chain, having approximately 20 to 250 ethylene glycol ether groups and approximately 10 to 100 propylene glycol ether groups in the usual ratio of 1 to 5 ethylene glycol moiety propylene glycol moiety; fatty acid esters of polyoxyethylene sorbitan; quaternary ammonium salts in the form of halides; quaternary ammonium salts in the form of methylsulphates; quaternary ammonium salts in the form of ethylsulphates; aminocarboxylic acids and salts thereof; aminosulphonic acids and salts thereof; nonylphenol ethoxylates; phosphated alkyl ethoxylates sodium fatty alcohol triethyoxysulfates; fatty alcohol ethoxylates; coconut monoethanol amides; coconut diethanolamides; coconut isopropanolamides; alkylbenzyldimethyl ammonium chlorides; and sodium alkyl benzene sulfonates; soap; sodium lauryl sulphate; sodium alkyl benzene sulphonate sodium cholate; sodium methyl oleoyl taurate and any mixture thereof.

16. The method of claim 11 wherein the combination further includes a foam promoting agent.

17. The method of claim 16 wherein the foam promoting agent is selected from the group consisting of methyl isobutyl carbinol, 4-methyl-2-pentanol, poly(propylene glycol) methyl ethers, glycerol, pine oil, cresylic acid, creosote, vegetable oils, epoxidised vegetable oils, epoxidised coconut oil, rape oil, soybean oil, soaps, proteins, extract of licorice root, extract of fatty acids, extract of sulphite liquors, starch, sodium carboxymethyl cellulose, methocel, carboxy vinyl polymers, sodium alginate, potassium alginate, ammonium alginate, xanthan gum, magnesium aluminum silicates, methyl cellulose, natural gums, gum arabic, clays, soap gels, lipophilic fatty acid esters, alum cocamide, cocamidoethyl betaine, cocamidopropyl betaine, cocamidopropyl hydroxysultaine, cocoamphodipropionic acid, coco-betaine, coco/oleamidopropyl betaine, coco-sultaine, cocoyl hydroxyethyl imidazoline, polyvinylpyrrolidone, polyox, cetyl betaine, decyl betaine, DEA-cocamphodipropionate, DEA-lauraminopropionate, disodium isostearyl sulphosuccinate, isopropyl stearate, lauramide, lauramidopropyl betaine, lauryl betaine, lauryl sultaine, myristamidopropyl betaine, myristaminopropionic acid, myristyl betaine, oleamidopropyl betaine, oleamidopropyl hydroxysultaine, oleyl betaine, palmamidopropyl betaine, palmitamidopropyl betaine, PEG-6 cocamide, PEG-3 lauramide, PEG-S lauramide, PEG-6 lauramide, sodium cocoamphoacetate, sodium cocoamphopropionate, sodium lauraminopropionate, sodium lauroamphopropionate, sodium lauroyl sarcosinate, sodium myristoamphoacetate, sodium myristoyl sarcosinate, TEA-hydrogenated tallow glutamate, TEA-lauraminopropionate, TEA myristaminopropionate or undecylenamidopropylamine oxide, alumina gel, and any mixture thereof.

18. The method of claim 11 wherein the oxidising agent is selected from the group consisting of a peroxide, hydrogen peroxide, zinc peroxide, benzoyl peroxide, potassium peroxide, sodium perborate, potassium perborate, oxone of the formula, sodium persulphate, sodium percarbonate, sodium hypochlorite, potassium hypochlorite, ammonium hypochionate, potassium percarbonate, ammonium percarbonate, ammonium persulphate, potassium persulphate, t-butyl hydroperoxide, magnesium monoperoxyphthalate, sodium peroxide, urea hydrogen peroxide, magnesium peroxide, calcium peroxide, and any mixture thereof.

19. The method of claim 11 wherein the combination comprises a combination selected from the group consisting of

| COMBINATION I | |
|---|---|
| Acid, optionally anhydrous, solid and in granulated or powdered form: | 5–90 wt % or mole % |
| Carbonate or bicarbonate, optionally anhydrous, solid and in granulated or powdered form: | 5–90 wt % or mole % |
| Surfactant, solid and in granulated or powdered form: | 0.1–90 wt % or mole % |

| COMBINATION II | |
|---|---|
| Acid, optionally anhydrous, solid and in granulated or powdered form: | 5–90 wt % or mole % |
| Carbonate or bicarbonate, optionally anhydrous, solid and in granulated or powdered form: | 5–90 wt % or mole % |
| Surfactant, solid and in granulated or powdered form: | 0.1–89.9 wt % or mole % |
| Oxidizing agent, solid and in granulated or powdered form: | 0.1–89.9 wt % or mole % |

| COMBINATION III | |
|---|---|
| Acid, optionally anhydrous, solid and in granulated or powdered form: | 5–90 wt % or mole % |
| Carbonate or bicarbonate, optionally anhydrous, solid and in granulated or powdered form: | 5–90 wt % or mole % |
| Surfactant, solid and in granulated or powdered form: | 0.1–89.9 wt % or mole % |
| Foam promoting agent, solid and in granulated or powdered form: | 0.1–89.9 wt % or mole % |

| COMBINATION IV | |
|---|---|
| Acid, optionally anhydrous, solid and in granulated or powdered form: | 5–90 wt % or mole % |
| Carbonate or bicarbonate, optionally anhydrous, solid and in granulated or powdered form: | 5–90 wt % or mole % |
| Surfactant, solid and in granulated or powdered form: | 0.1–89.9 wt % or mole % |
| Foam promoting agent, solid and in granulated or powdered form: | 0.1–89.9 wt % or mole % |
| Oxidizing agent, solid and in granulated or powdered form: | 0.1–89.9 wt % or mole % |

COMBINATION V

| | |
|---|---|
| Acid, optionally anhydrous, solid and in granulated or powdered form: | 5–90 wt % or mole % |
| Carbonate or bicarbonate, optionally anhydrous, solid and in granulated or powdered form: | 5–90 wt % or mole % |
| Surfactant, solid and in granulated or powdered form: | 0.1–89.7 wt % or mole % |
| Foam promoting agent, solid and in granulated or powdered form: | 0.1–89.7 wt % or mole % |
| Oxidising agent, solid and in granulated or powdered form: | 0.1–89.7% or mole % |
| Perfume and Other additives, solid and in granulated or powdered form and | 0.1–89.7 wt % or mole % |

COMBINATION VI

| | |
|---|---|
| Acid, solid and in granulated or powdered form: | 5–90 wt % or mole % |
| Carbonate or bicarbonate, solid and in granulated or powdered form: | 5–90 wt % or mole % |
| Surfactant, solid and in granulated or powdered form: | 0.1–90 wt % or mole % |

20. The method of claim 11 wherein the combination comprises:
(i) 5–90 wt % or mole % of an acid, optionally anhydrous, selected from the group consisting of citric acid, tartaric acid, boric acid, saccharic acid, tartronic acid, oxalic acid, succinic acid, tartaric acid, salicylic acid, adipic acid, and ascorbic acid,
(ii) 5–90 wt % or mole % of an alkaline effervescent compound, optionally anhydrous, selected from the group consisting of sodium hydrogen carbonate, potassium bicarbonate, and ammonium bicarbonate,
(iii) 0.1–89.8 wt % or mole % of a surfactant selected from the group consisting of sodium methyl oleoyl taurate, sodium lauryl sulphate and sodium alkyl benzene sulphonate,
(iv) 0.1–89.8 wt % or mole % of a foam promoting agent selected from the group consisting of xanthan gum, sodium alginate, potassium alginate and ammonium alginate,
(v) 0.1–89.9 wt % or mole % of an oxidising agent selected from the group consisting of sodium perborate, potassium perborate, oxone of the formula, sodium persulphate, sodium percarbonate, sodium hypochlorite, potassium hypochlorite, ammonium hypochlorite, potassium percarbonate, ammonium percarbonate, ammonium persulphate, potassium persulphate, and urea hydrogen peroxide.

21. The method of claim 11 wherein the aqueous based medium is selected from the group consisting of water in a toilet bowl, urinal, septic tank, sewage containing water, foul water, aqueous industrial waste, aqueous grease traps and sullage pits.

22. The combination of claim 1 wherein the combination is in a form selected from the group consisting of powder, granules, tablets, capsules, beads, and mixtures thereof.

23. The combination according to claim 1, further comprising a foam promoting agent in solid form.

24. The combination according to claim 23, wherein the foam promoting agent is xanthan gum.

25. The combination according to claim 23, wherein said foam forming surfactant is sodium methyl oleoyl taurate.

26. A combination capable of forming an odor barrier comprising a stable foam, the combination comprising:
(i) a first component comprising anhydrous sodium hydrogen carbonate in solid form,
(ii) a second component comprising anhydrous citric acid in solid form,
(iii) an oxidizing agent in solid form, and
(iv) xanthan gum in solid form,
wherein at least one of the first component and the second component comprises sodium methyl oleoyl taurate in solid form,
the first component reacts with the second component to form a stable foam odor barrier which traps/blocks odors emanating from an aqueous based medium,
together with a multi-compartmented air-tight and moisture-tight container,
wherein the first component and the second component of the combination are packaged in the multiple-compartmented, air-tight and moisture-tight container, thereby separating the first and second components in the packaging to prevent reaction, until the combination is required to form an odour barrier by addition to an aqueous medium.

27. The combination according to claim 26 wherein the oxidizing agent is selected from the group consisting of sodium persulfate, sodium percarbonate, potassium percarbonate, ammonium percarbonate, ammonium persulfate, potassium persulfate, and any mixture thereof.

28. The combination according to claim 26, wherein the oxidizing agent is sodium percarbonate.

29. The combination according to claim 8, wherein the oxidizing agent is selected from the group consisting of sodium persulfate, ammonium persulfate, potassium persulfate and any mixtures thereof.

30. The method according to claim 18, wherein the oxidizing agent is selected from the group consisting of sodium persulfate, ammonium persulfate, potassium persulfate and any mixtures thereof.

31. The combination according to claim 3, wherein the acid is selected from the group consisting of citric acid, boric acid, stearic acid, palmitic acid, glucuronic acid, mandelic acid, saccharic acid, tartronic acid, beta-hydroxybutyric acid, malic acid, mitramalic acid, mucic acid, lactic acid, oxalic acid, succinic acid, salicylic acid, ascorbic acid and any mixture thereof.

32. The combination of claim 5, wherein the foam forming agent is selected from the group consisting of coconut monoethanlamide, coconut monoethanolamide, sodium lauryl sulfate, and sodium methyl oleyl taurate.

33. The combination of claim 7, wherein the foam promoting agent selected from the group consisting of starch, sodium carboxymethyl cellulose, methocel, sodium alginate, potassium alginate, ammonium alginate, xanthan gum, magnesium aluminum silicates, methylcellulose, gum arabic, clays, polyvinylpyrrolidone, and PEG-6 lauramide.

* * * * *